(12) United States Patent
Elgaard Pederson (10) Patent No.: US 10,300,253 B2
(45) Date of Patent: May 28, 2019

(54) WEEPING BALLOON WITH FLOW CHANNELS FOR REDUCED INFUSION PRESSURE

(71) Applicant: Cook Medical Technologies LLC, Bloomington, IN (US)

(72) Inventor: Per Elgaard Pederson, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 49 days.

(21) Appl. No.: 15/336,017

(22) Filed: Oct. 27, 2016

(65) Prior Publication Data

US 2017/0128703 A1    May 11, 2017

Related U.S. Application Data (60) Provisional application No. 62/253,241, filed on Nov. 10, 2015.

(51) Int. Cl.
*A61M 25/10* (2013.01)

(52) U.S. Cl.
CPC .... *A61M 25/1011* (2013.01); *A61M 25/1002* (2013.01); *A61M 25/1029* (2013.01); *A61M 2025/1004* (2013.01); *A61M 2025/105* (2013.01); *A61M 2025/1013* (2013.01)

(58) Field of Classification Search
CPC .......... A61M 25/1011; A61M 25/1002; A61M 25/1029
USPC ................................................... 604/101.02
See application file for complete search history.

(56) References Cited

U.S. PATENT DOCUMENTS

| | | |
|---|---|---|
| 4,437,856 A | 3/1984 | Valli |
| 5,236,659 A | 8/1993 | Pinchuk |
| 5,336,178 A | 8/1994 | Kaplan et al. |
| 5,792,105 A | 8/1998 | Lin et al. |
| 7,094,765 B1 | 8/2006 | Iversen et al. |
| 8,034,022 B2 | 10/2011 | Boatman |

(Continued)

FOREIGN PATENT DOCUMENTS

WO    WO 2009/036135 A1    3/2009

OTHER PUBLICATIONS

International Patent Application PCT/US2016/059103 Search Report and Written Opinion dated Mar. 20, 2017. 19 pages.

(Continued)

*Primary Examiner* — Phillip A Gray
(74) *Attorney, Agent, or Firm* — Woodard, Emhardt, Henry, Reeves and Wagner LLP (57) ABSTRACT

Method of forming a multiple balloon catheter includes extruding a tube and a plurality of ribs through a die to form a monolithic element that spans between first and second ends with the plurality of ribs extending along the length of the tube to define a corresponding number of a plurality of channels that extend along the length of the tube. Positioning a portion of the tube into a mold and constricting a proximal end portion and a distal end portion of the tube that is positioned in the mold. Inflating the tube to produce an inner balloon having a body portion that spans between proximal and distal end portions and cutting the inner balloon to separate the inner balloon from a remainder of the tube. Disposing an outer balloon including a plurality of holes around the inner balloon and aligning the plurality of holes with the plurality of channels.

19 Claims, 5 Drawing Sheets

(56) References Cited

U.S. PATENT DOCUMENTS

| | | |
|---|---|---|
| 8,162,880 B2 | 4/2012 | Jayaraman |
| 8,348,890 B2 | 1/2013 | Gerrans et al. |
| 8,454,637 B2 | 6/2013 | Aggerholm et al. |
| 8,591,461 B2 * | 11/2013 | Boatman ............ A61M 25/1011 604/101.01 |
| 2006/0269587 A1 | 11/2006 | Iversen et al. |
| 2009/0254064 A1 | 10/2009 | Boatman |
| 2011/0160756 A1 | 6/2011 | Aggerholm et al. |
| 2012/0130407 A1 | 5/2012 | Aggerholm et al. |
| 2014/0088624 A1 | 3/2014 | Burton et al. |
| 2014/0155927 A1 | 6/2014 | Burton |

OTHER PUBLICATIONS

International Patent Application PCT/US2016/059103 Partial Search Report dated Jan. 25, 2017. 8 pages.

* cited by examiner

WEEPING BALLOON WITH FLOW CHANNELS FOR REDUCED INFUSION PRESSURE

CROSS-REFERENCE TO RELATED APPLICATIONS

This application claims the benefit of U.S. Provisional Application No. 62/253,241 filed Nov. 10, 2015, which is hereby incorporated by reference.

BACKGROUND

The present application relates to medical catheters configured to release a therapeutic agent. More particularly, the present application relates to medical multiple balloon catheters that include having an inner balloon and an outer balloon and one or more flow channels therebetween.

In cell therapy, it is important to keep the infusion pressure low in order to reduce the physical stress on the cells. In some weeping balloon designs, the inner balloon is inflated to approximately 2 ATM and a significant part of the infusion pressure is used to create a flow path between the pressurized inner balloon and the perforated outer balloon. If the infusion pressure is too high, then the physical stress on the cells in cell therapy and other forms of medical treatment is too high. Moreover, the high cost to manufacture medical multiple balloon catheters that effectively deliver cell therapy with a low infusion pressure is also a concern for many consumers.

Thus, there is a need for improvement in this field.

SUMMARY

The present invention seeks to provide an improved method of forming a multiple-balloon intraluminal fluid delivery catheter for delivering a fluid into a body vessel. The method includes extruding a tube and a plurality of ribs through a die to form a monolithic single element that has a length that spans between a first end and a second end with the plurality of ribs extending along the length of the tube, the plurality of ribs defining a corresponding number of a plurality of channels that extend along the length of the tube. The method further includes positioning a portion of the tube into a mold, the mold having a corresponding number of grooves sized and positioned to receive the plurality of ribs on the tube and constricting a proximal end portion near the first end and a distal end portion near the second end of the portion of the tube that is positioned in the mold. Thereafter the method includes inflating the tube to produce an inner balloon, the inner balloon having a body portion that spans between the proximal end portion and the distal end portion and cutting the inner balloon near the proximal end portion and near the distal end portion to separate the inner balloon from a remainder of the tube. Lastly the method includes disposing an outer balloon around the inner balloon, the outer balloon being movable between a compressed configuration and an expanded configuration, the outer balloon including a plurality of holes.

Optionally, the method includes aligning the plurality of holes of the outer balloon with the plurality of channels on the inner balloon. According to one embodiment, the method includes heating the portion of the tube in the mold and stretching the portion of the tube in the mold. In another embodiment, the constricting includes radially compressing the proximal end portion and the distal end portion. In yet another embodiment, the method includes mounting the inner balloon on a catheter shaft and mounting the outer balloon around at least a portion of the inner balloon. The method may reduce the height of the plurality of ribs by a linear amount along the proximal end portion and the distal end portion to reduce the stiffness of the plurality of ribs. Further the method may reduce the height of the plurality of ribs by laser cutting or grinding a portion of each of the plurality of ribs. The method may reduce the height of the plurality of ribs while inflating the tube to produce the inner balloon. The method may cut the inner balloon before the reducing the height of the plurality of ribs.

In one embodiment, a multiple balloon intraluminal fluid delivery catheter for delivering a fluid into a body vessel includes a catheter shaft extending along a longitudinal axis from a proximal end to a distal end, the catheter shaft including an inflation lumen to deliver an inflation fluid and a fluid delivery lumen to deliver said fluid and an inner balloon having a middle portion that spans between a proximal end portion and a distal end portion, the inner balloon having an exterior surface with a plurality of ridges thereon that together span longitudinally from the proximal end portion to the distal end portion, each of the plurality of ridges having a height that is constant along the middle portion, the inner balloon mounted on the distal end of the catheter shaft and in communication with the inflation lumen, the inner balloon being movable between a deflated configuration and an inflated configuration. The catheter includes an outer balloon mounted around the inner balloon, the outer balloon having a middle portion that spans between a proximal end and a distal end, the outer balloon being movable between a compressed configuration and an expanded configuration, the outer balloon including a plurality of holes. The inner balloon and the outer balloon are configured and oriented such that a plurality of flow channels are defined when the inner balloon is in the inflated configuration and the outer balloon is in the expanded configuration and a portion of each of the plurality of ridges that spans along the middle portion engage an inner surface of the outer balloon, the inflated configuration of the inner balloon and the expanded configuration of the outer balloon defines an annular lumen there between, the annular lumen and the plurality of flow channels being in communication with the fluid delivery lumen and the plurality of holes such that the annular lumen and the plurality of flow channels are configured to promote delivery of said fluid through the plurality of holes, the annular lumen having a constant cross-sectional area along the longitudinal axis.

In one embodiment of the multiple balloon intraluminal fluid delivery catheter, the plurality of ridges along the middle portion of the inner balloon engages the inner surface of the outer balloon. Alternatively, the multiple balloon intraluminal fluid delivery catheter may include the plurality of ridges along the middle portion, the proximal end portion, and the distal end portion of the inner balloon engage the inner surface of the outer balloon. The multiple balloon intraluminal fluid delivery catheter may include the plurality of holes that are uniformly spaced along the longitudinal axis. The multiple balloon intraluminal fluid delivery catheter may also have the plurality of flow channels that have a constant cross-sectional area along the longitudinal axis.

Further forms, objects, features, aspects, benefits, advantages, and embodiments of the present invention will become apparent from a detailed description and drawings provided herewith.

DESCRIPTION OF THE SELECTED EMBODIMENTS

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible" refers to a material that is substantially non-toxic in the in vivo environment of its intended use and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, and/or immunogenicity. A biocompatible structure or material, when introduced into a majority of patients, will not cause an undesirably adverse, long-lived or escalating biological reaction or response and is distinguished from a mild, transient inflammation which typically accompanies surgery or implantation of foreign objects into a living organism.

As used herein, the term "body vessel" means any body passage lumen that conducts fluid, including but not limited to blood vessels, esophageal, intestinal, biliary, urethral, and ureteral passages.

The medical devices of the embodiments described herein can be oriented in any suitable absolute orientation with respect to a body vessel. The recitation of a "first" direction is provided as an example. Any suitable orientation or direction can correspond to a "first" direction. For example, the first direction can be a radial direction in some embodiments.

Figure 1:
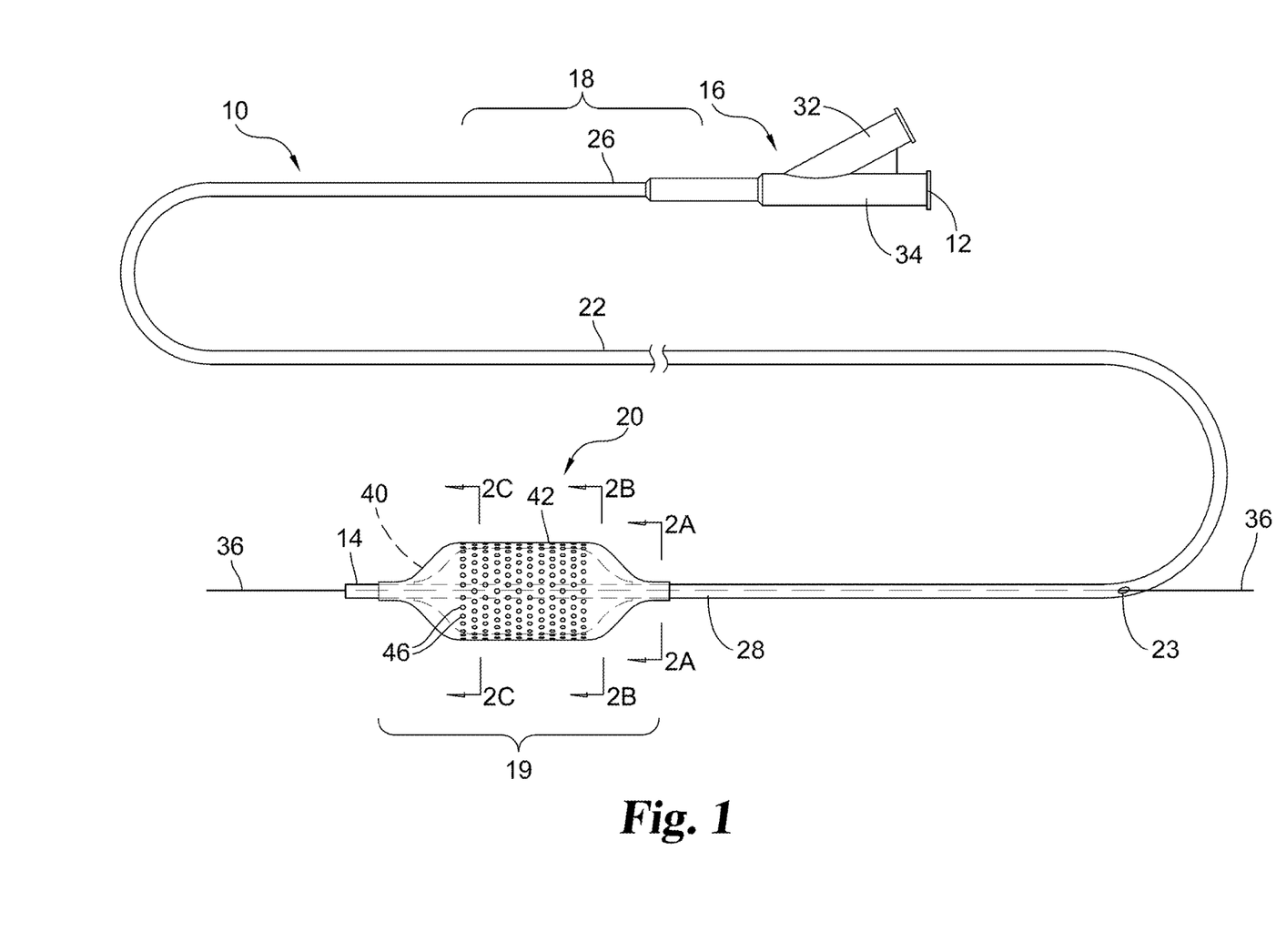
FIG. 1 is a front view of one embodiment of a multiple balloon catheter.
Figure 2A:
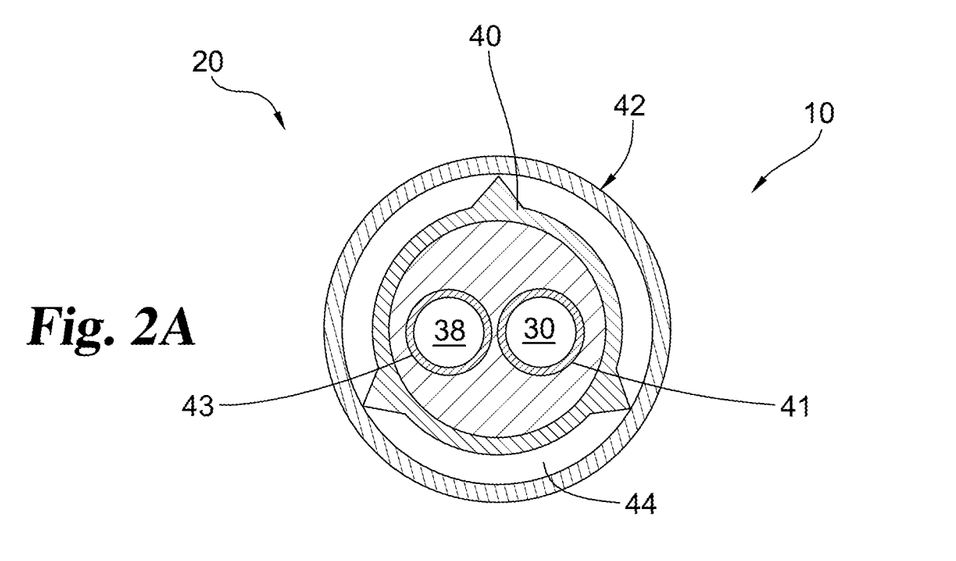
FIG. 2A is a transverse cross-sectional view along line 2A-2A of the multiple balloon catheter shown in FIG. 1.
Figure 2B:
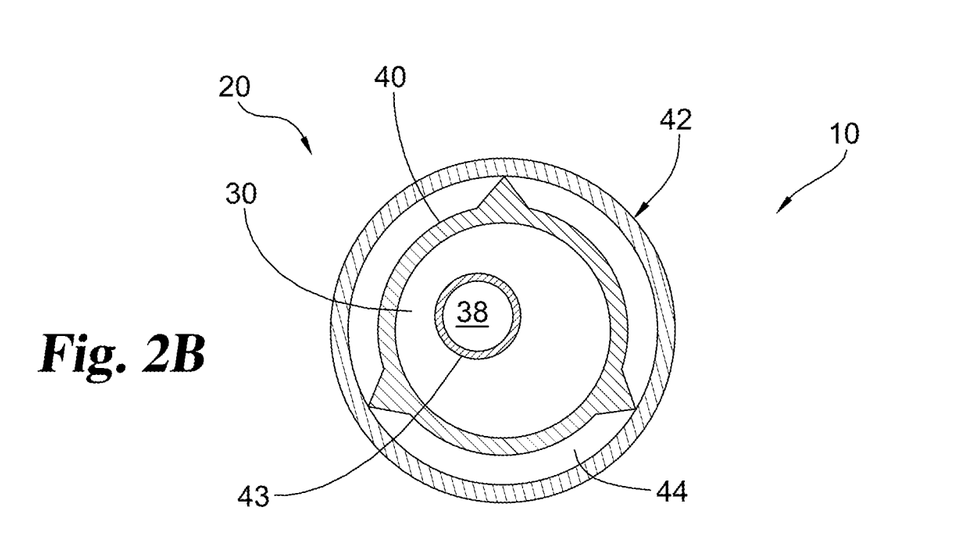
FIG. 2B is a transverse cross-sectional view along line 2B-2B of the multiple balloon catheter shown in FIG. 1.
Figure 2C:
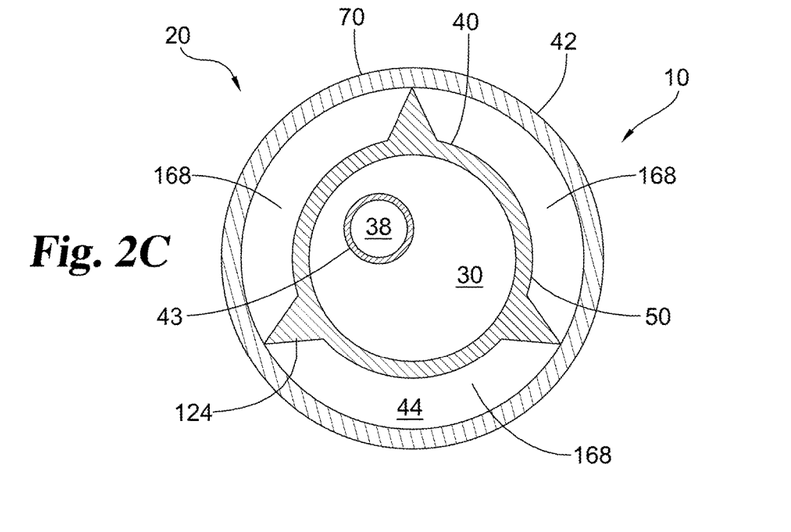
FIG. 2C is a transverse cross-sectional view along line 2C-2C of the multiple balloon catheter shown in FIG. 1.

FIGS. 1, 2A, 2B, 2C, and 3 illustrate an example embodiment of a medical device comprising a multiple balloon catheter 10 or weeping balloon catheter made with the present disclosure. The multiple balloon catheter 10 extends from a proximal end 12 to a distal end 14. The multiple balloon catheter 10 includes a manifold 16 located near a proximal end region 18 of the multiple balloon catheter 10 and a multiple balloon assembly 20 at a distal end region 19 of the multiple balloon catheter 10. The manifold 16 is operatively connected to a catheter shaft 22 in the proximal end region 18. The catheter shaft 22 extends from a proximal end 26 to a distal end 28. The manifold 16 can include an injection port 32 and an inflation port 34. As shown in FIGS. 2A, 2B, and 2C, the catheter shaft 22 can include an inflation lumen 30, a fluid delivery lumen 33 (FIG. 3) spaced from the inflation lumen 30, and a wire guide lumen 38. The catheter shaft 22 can also include one or more conventional fittings and/or adapters between the manifold 16 and the proximal end 26 of the catheter shaft 22. The multiple balloon catheter 10 can be a "short wire" system having a wire guide port 23 within an intermediate region of the catheter shaft 22, providing access to the wire guide lumen 38 extending through the catheter shaft 22 from the wire guide port 23 to the distal end 14 of the multiple balloon catheter 10, as shown in FIG. 1. Optionally, the multiple balloon catheter 10 can be an "over the wire" system with the wire guide port 23 positioned as part of the manifold 16. In this alternate embodiment, the manifold 16 includes the wire guide port 23 in addition to the inflation port 34 and the injection port 32.

The multiple balloon catheter assembly 20 includes a perforated outer balloon 42 radially disposed around an inner balloon 40. The inner balloon 40 is non-porous and in fluid communication with the inflation port 34 through the body of the catheter shaft 22. The outer balloon 42 includes a plurality of holes 46 and is in fluid communication with the injection port 32 through the catheter shaft 22 and separated from both the inner balloon 40 and the inflation port 34. In the illustrated embodiment, the individual holes within the plurality of holes 46 are uniformly positioned along the outer balloon 42. In other embodiments, the individual holes within the plurality of holes 46 can have an alternative distribution such as variable spacing, grouped spacing, or evenly spaced.

Figure 3:
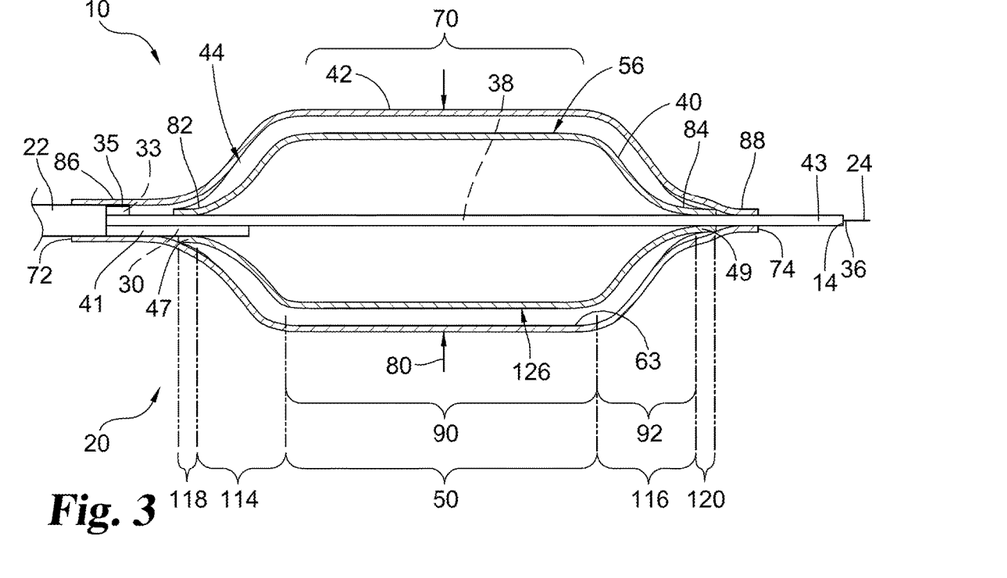
FIG. 3 is a partial longitudinal cross-sectional view of the multiple balloon catheter shown in FIG. 1.

In one embodiment shown in FIG. 3, the inner balloon 40 has a generally uniform cross-sectional area moving distally along a longitudinal axis 24, and the outer balloon 42 has a corresponding cross-sectional area that is similar to the inner balloon 40. The profile and cross-sectional area of both the inner balloon 40 and the outer balloon 42 is described in more detail below. Illustrated in FIG. 3, an annular balloon fluid delivery lumen 44 for receiving a therapeutic agent or fluid, such as a diagnostic media, from the injection port 32 via the fluid delivery lumen 33 can be formed between the inner balloon 40 and the outer balloon 42. Both the inner balloon 40 and the outer balloon 42 can be sealed to the distal end 28 of the catheter shaft 22. The multiple balloon assembly 20 can be translated over a wire guide 36 that is shown extending from the wire guide port 23, through the catheter shaft 22 and extending through the distal end 14 of the multiple balloon catheter 10. The multiple balloon assembly 20 is typically provided separately from the wire guide 36, an introducer sheath (not shown) or other devices typically used to insert the multiple balloon assembly 20 within a body vessel.

The catheter shaft 22 of the multiple balloon catheter 10 is shaped and configured for the intended use in a body vessel. In the illustrated embodiment, the catheter shaft 22 includes the wire guide lumen 38 configured to house a wire guide 36. In one form, the wire guide lumen 38 has an inside diameter of about approximately 0.5 mm but can be smaller from about 0.25 mm or larger to about 1.0 mm. The overall length of the catheter shaft 22 can be approximately 110 cm to about 180 cm or smaller from about 50 cm to about 80 cm. The outside diameter of the catheter shaft 22 is typically approximately 1-1.5 mm, but can be up to about 3.5 mm. Further details regarding the manufacturing and/or assembling of the catheter shaft 22 are described in U.S. PCT Application Number US2008/75970 filed on Sep. 11, 2008, published as WO 2009/036135 A1, which is incorporated by reference.

FIG. 2A is a transverse cross-sectional view of the multiple balloon assembly 20 along line 2A-2A in FIG. 1 showing a proximal end of the multiple balloon assembly 20 of the multiple balloon catheter 10. The inner balloon 40 includes a tubular member 41 defining the inflation lumen 30 and a tubular member 43 defining the wire guide lumen 38. In this embodiment, the inflation lumen 30 and the fluid delivery lumen 33 (not shown in FIG. 2A) are in isolation from one another. The fluid delivery lumen 33 is in fluid communication with the annular balloon fluid delivery lumen 44, which is shown between the outer balloon 42 and the inner balloon 40.

FIG. 2B is a transverse cross-sectional view of the multiple balloon assembly 20 along line 2B-2B in FIG. 1 that is distally located from the line 2A-2A, showing a proximal portion of the multiple balloon assembly 20 of the multiple balloon catheter 10 in the inflated configuration. The inner balloon 40, shown as tapered and described below in more detail, defines the inflation lumen 30 extending radially around the tubular member 43 that defines the wire guide lumen 38. The annular balloon fluid delivery lumen 44 is shown to be in between the outer balloon 42 and the inner balloon 40. The cross-sectional area or diameter of the annular balloon fluid delivery lumen 44 is generally constant along the length of the inner balloon 40.

FIG. 2C is a transverse cross-sectional view of the multiple balloon assembly 20 along line 2C-2C in FIG. 1 that is distally located from the line 2B-2B, showing a body portion 50 and a middle portion 70 of the multiple balloon assembly 20 of the multiple balloon catheter 10 in the inflated configuration. The inner balloon 40 defines the inflation lumen 30 extending radially around the tubular member 43 that defines the wire guide lumen 38. The holes 46 are in fluid communication with the annular balloon fluid delivery lumen 44, which is shown between the outer balloon 42 and the inner balloon 40.

Referring to FIG. 3, the inner balloon 40 having a proximal end 47 and a distal end 49 is mounted at the distal end 14 of the catheter shaft 22. The inner balloon 40 is inflatable between a deflated configuration and an inflated configuration. The inflation lumen 30 defined by the tubular member 41 of the catheter shaft 22 is in fluid communication with the inner balloon 40. The inflation of the inner balloon 40 can be accomplished by any suitable means known in the art, e.g., by introducing an inflation fluid (e.g., air, saline, etc.) through the inflation lumen 30 into the inner balloon 40.

Figure 4:
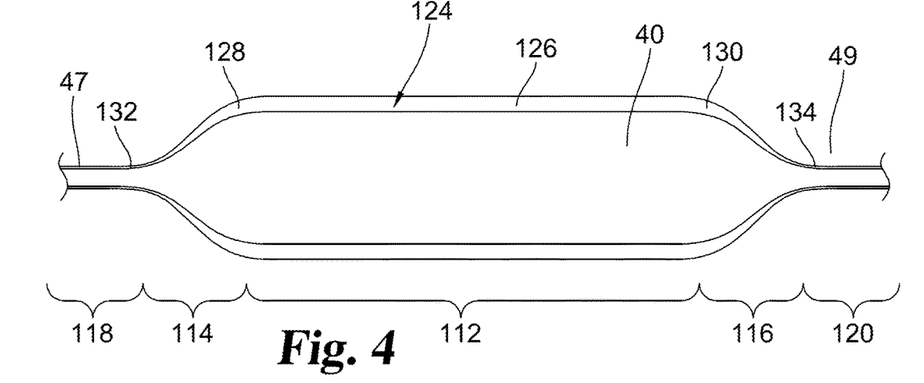
FIG. 4 is a partial longitudinal cross-sectional view of an inner balloon before the inner balloon is assembled with the outer balloon shown in FIG. 3.

Referring to FIG. 4, the inner balloon 40 includes a generally cylindrical and straight body portion 112 which extends along a longitudinal axis of the inner balloon 40. At the proximal end of the body portion 112 there is a proximal end portion 114 adjacent a proximal neck portion 118. At the distal end of the body portion 112 there is a distal end portion 116 adjacent a distal neck portion 120. The proximal end portion 114 and distal end portion 116 are illustrated as conical; however, the proximal and distal end portions 114 and 116 will typically be slightly rounded since they form part of the inflatable structure of the inner balloon 40.

The proximal end 47 of the proximal neck portion 118 connects with the catheter shaft 22 and the distal end 49 of the distal neck portion 120 connects with the tubular member 43 which are typically configured in a fluid tight manner.

As described below in further detail, the portions 112-120 of the inner balloon 40 are typically formed from a common raw tubing which is inflated under heating so as to stretch into the shape shown in FIG. 4. In one embodiment, these portions 112-120 of the inner balloon 40 can be formed from the same material, although they may have different wall thicknesses as a result of the different extents to which the raw tubing is inflated, that is stretched during formation of the balloon. Typically, the body portion 112 will have a thinner balloon wall, whereas the proximal end portion 114 and the distal end portion 116 will have a wall thickness which increases in the direction of reduction of their taper. The proximal neck portion 118 and the distal neck portion 120 will have the thickest walls. It is to be appreciated that these differences in thickness may be minimal and thus of no or little material effect to the operating characteristics of the inner balloon 40. In some circumstances, additional manufacturing steps may be performed to even out these walls thicknesses. Additional details regarding another manufacturing process and/or assembling of the inner balloon 40 are described in U.S. application Ser. No. 12/964,055 filed on Dec. 9, 2010, published as US 2011/0160756 A1, which is incorporated by reference.

The inner balloon 40 also includes a plurality of ridges 124 which extend from the distal neck portion 120 to the proximal neck portion 118. In the illustrated embodiment there are three ridges 124, although there could be one or more than three in other embodiments. In this example, the ridges 124 extend substantially linearly along the axis of the balloon and are substantially equally spaced around the circumference of the inner balloon 40. In an alternative embodiment, the ridges are placed on an interior surface of the outer balloon as described in more detail below (see FIG. 9). The ridges 124 may also be positioned on both of an outside surface of the inner balloon 40 and an interior surface 63 of the outer balloon 42 and can be arranged in an alternating or some other pattern.

Each ridge 124 has a ridge body portion 126 which extends along the body portion 112 of the inner balloon 40. In the preferred embodiment, the ridge body portion 126 of each ridge 124 has a substantially constant height for the length of the body portion 112, although in other embodiments this height could vary. Each ridge 124 includes a proximal tapering section 128 which extends from the ridge body portion 126 along the proximal end portion 114 and a distal tapering section 130 which extends from the ridge body portion 126 along the distal end portion 116. Each ridge 124 includes a proximal outer region 132 adjacent the proximal tapering section 128 and a distal outer region 134 adjacent the distal tapering section 130 wherein the proximal and the distal outer regions 132, 134 extend over the proximal and the distal neck portions 118, 120, respectively. Alternative embodiments can include alternative configurations for the proximal and the distal outer regions 132, 134 such that the proximal and the distal outer regions 132, 134 are not visible or may have been removed, for instance by being pressed or molded into the proximal and the distal neck portions 118, 120 or by being cut away, as described below.

The proximal and the distal tapering sections 128, 130 of each ridge 124 taper from a height that is consistent across or along the ridge body portion 126 to a lower height along the direction of taper of the proximal and the distal neck portions 118, 120. In one embodiment, the proximal and the distal tapering sections 128, 130 of each ridge 124 taper to a zero height. This reduction in height of the ridges 124 as the inner balloon 40 narrows enhances the flexibility of the inner balloon 40 at the proximal and the distal neck portions 118, 120 and also ensures that there is no abrupt change in the height of the ridges 124.

In the illustrated embodiment, the proximal and the distal tapering sections 128, 130 of each ridge 124 exhibit a gradual, linear, reduction in height. Alternatively, the reduction in height of the proximal and the distal tapering sections 128, 130 could vary or have a different overall profile. In yet other embodiments, the proximal and the distal tapering sections 128, 130 of each ridge 124 have a constant height and do not taper to a lower height.

Figure 5:
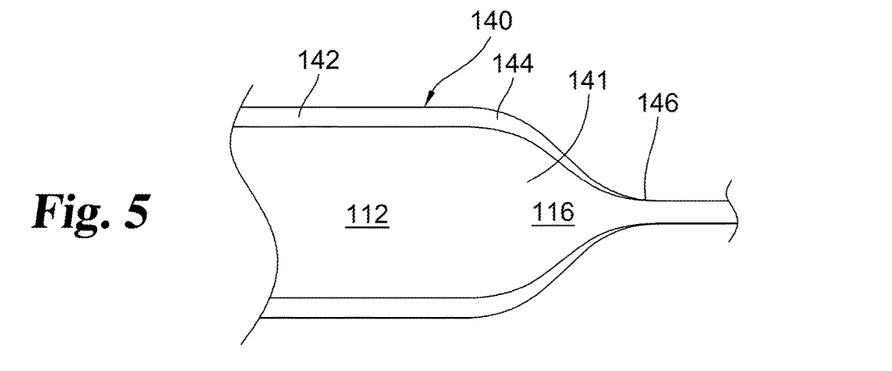
FIG. 5 is a partial longitudinal cross-sectional view of a second embodiment of an inner balloon.

Turning now to FIG. 5, there is shown an alternative partial embodiment of ridges 140 on an inner balloon 141. In this embodiment, the ridges 140 extend from a central uniform section 142 along the body portion 112 to a tapering section 144 which gradually tapers all the way down the distal end portion 116 to the distal neck portion 120. Each of the ridges 140 includes a point of contact 146 of the ridges 140 which lies along the distal neck portion 120 which does not have a height relative to an outer surface of the distal neck portion 120. In other words, the point of contact 146 is substantially flat with an outer surface of the distal neck portion 120.

Figure 6:
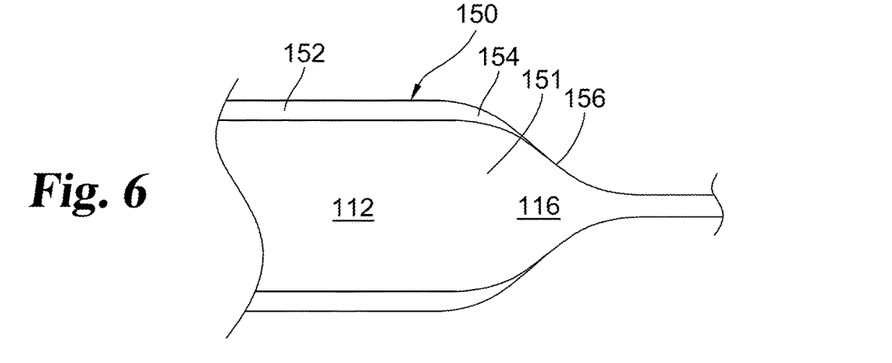
FIG. 6 is a partial longitudinal cross-sectional view of a third embodiment of an inner balloon.

FIG. 6 shows another embodiment of a ridge 150 on an inner balloon 151 wherein the ridge 150 includes a tapering section 154, which extends from a central section 152 along the distal end portion 116 and tapers or is reduced in height to a point of contact 156. The point of contact 156 has no height and is substantially flat or flush with an outer surface of the distal neck portion 120. The point of contact 156 is located about mid-way along the distal end portion 116.

In other embodiments, the tapering sections 130, 144, and 154 can have tapers which are other than linear such as rounded, stepped, curved, parabolic, or other geometrical shapes. The ridges 124, 140, 150 may be slightly rounded or curved at the junction between the body portion 112 and the proximal and the distal end portions 114, 116, caused by rounding of the inner balloon 40 during inflation.

Figure 7:
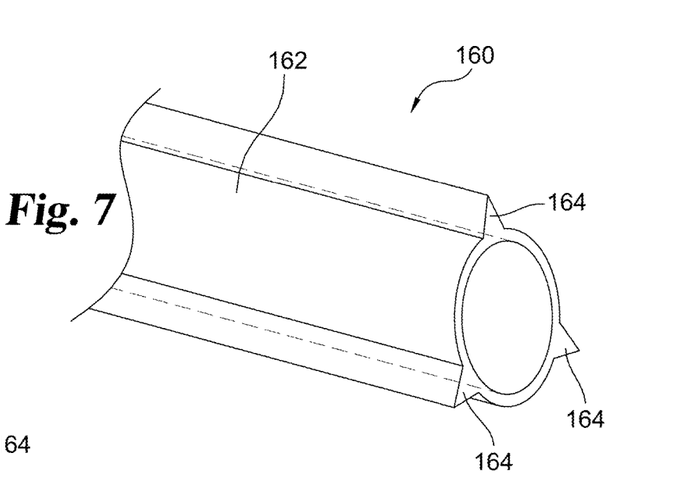
FIG. 7 is a perspective end view of an embodiment of raw material tubing used to produce the inner balloons of FIGS. 1, 2A-2C, 3, 4, 5, and 6.
Figure 8:
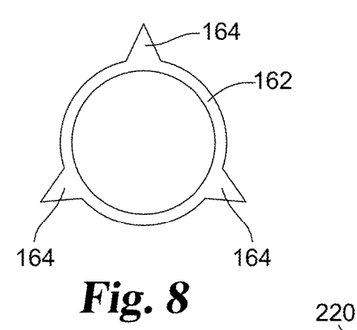
FIG. 8 is an end view of the raw material tubing of FIG. 7.

FIGS. 7 and 8 show an embodiment of raw tubing 160 used for the manufacture of the inner balloons 40 described in this application. The raw tubing 160 is advantageously a continuous length of tubing having a substantially circular cylindrical tube portion 162 from which extend radially outwardly a plurality of ribs 164. In FIGS. 7 and 8 the raw tubing 160 has three ribs 164 extending linearly along the outside of the tube 162, although the number will correspond to the number of ridges desired. The arrangement of the ribs 164 will also be dependent upon the desired shape of the ridges of the inner balloon 40. For instance, for ridges which extend at least partially helically around the inner balloon 40, the ribs 164 would also be at least partially helical.

In the preferred embodiment, the ribs 164 are formed to have a generally triangular or otherwise converging shape in axial cross-section, as apparent from FIGS. 7 and 8, and are preferably made of the same material as the tube 162. In one embodiment, the ribs 164 and tube 162 are extruded together, such that they are a single integral component piece with no distinction in terms of material. It is not excluded, however, that the ribs 164 could be made from a different material than that of the tube 162, for instance a material which is less flexible.

During manufacture, the raw tubing 160 is inflated in a suitable mold under heat so as to stretch the central part of the raw tubing 160 to form the body portion 112 and the proximal and the distal end portions 114, 116 of the inner balloon 40, while the proximal and the distal end portions 114, 116 of the raw tubing 160 are held radially compressed so as not to inflate and to form the proximal and the distal neck portions 118, 120.

In one embodiment, the ribs 164 are kept substantially intact during inflation of the raw tubing 160. In one embodiment, a central part of the mold which receives body portion 112 includes a plurality of grooves that are sized to receive the ribs 164 wherein one of the grooves receives one of the ribs 164 therein to preserve the shape of the ribs 164 during inflation of the raw tubing 160. At the end of the inflation stage, the portions of the ribs 164 which extend along the proximal and the distal neck portions 118, 120 of the just formed inner balloon 40 are then reduced in height, preferably by laser cutting or otherwise by ablation, grinding or other suitable method. In another embodiment, the portions of the ribs 164 which overlie the zones of the raw tubing which form the proximal and the distal neck portions 118, 120 and the proximal and the distal end portions 114, 116 are squashed during the balloon inflation process. Specifically, the conical portions of the mold which form the proximal and the distal tapering sections 128, 130 have no or reduced grooves to accommodate the ribs 164 of the raw tubing 160, as a result of which during the heating and inflation stages the ribs 164 are softened and heat squashed into the wall of the inner balloon 40. Laser cutting can also be used to cut the ribs 164 as it minimizes damage to the inner balloon or ridge material and is accurate.

The body portions 126, 142, 152 of the ridges may be a non-uniform or variable height or a constant non-changing height. The body portions 126, 142, 152 may have non-uniform heights, may bulge outwardly towards their middle, may reduce in height towards their middle, and may have a plurality of notches along their length.

Although there are described a number of embodiments above, these are not to be understood as limiting the scope of the inner balloons 40, 141, or 151 taught herein. For instance, even though the primary embodiments described above have three ridges extending longitudinally along the length of the inner balloon and substantially equally spaced circumferentially around the inner balloon, other embodiments are possible. For instance, a different number of ridges could be provided. Similarly, the ridges could be arranged non-linearly with respect to the axis of the inner balloon, such as helically along at least the body portion of the inner balloon. In other embodiments, the ridges could be unevenly spaced around the circumferential extent of the inner balloon. Various other arrangements are possible.

To assemble the inner balloon 40 with the outer balloon 42, the inner balloon 40 is mounted on and bonded or otherwise attached to the distal end of the catheter shaft 22. Next, the inner balloon 40 is pleated and folded. Turning now to the outer balloon 42 illustrated in FIG. 3, the outer balloon 42 is mounted on the distal end of the catheter shaft 22. The outer balloon 42 is mounted around at least a portion of the inner balloon 40, but preferably mounted entirely around the inner balloon 40, with the outer balloon 42 enclosing the inner balloon 40. The outer balloon 42 is then pleated and folded.

The outer balloon 42 includes a working length or a middle portion 70 between a proximal end 72 and a distal end 74. The outer balloon 42 is moveable between a compressed configuration and an expanded configuration. Preferably, the geometry, material and configuration of the outer balloon 42 are selected to withstand an internal pressure of a therapeutic agent and the inflation of the inner balloon 40 without any rupture.

Referring to both the inner balloon 40 and the outer balloon 42 in FIG. 3, an inflated outer diameter 56 of the inner balloon 40 spans along the length of the ridge body portion 126 wherein the outer diameter 56 corresponds to an outer edge of ridge 124 that also engages or contacts the interior surface 63 of the outer balloon 42. A flow channel 168 (illustrated in FIG. 2C) is created by the contact of two adjacent ridges 124 with the interior surface 63 of the outer balloon 42. In this particular embodiment, the flow channel 168 runs the length of the ridge body portion 126 and the body portion 50 wherein the inner balloon 40 and the outer balloon 42 maintain contact with one another. As such, the flow channel 168 extends from the ridge body portion 126 to the tapering sections 128, 130 and from the body portion 50 to the proximal end portion 114 and the distal end portion 116. In other embodiments, the flow channel 168 may have a shorter or longer length depending whether the portions of the inner balloon 40 and the outer balloon 42 that are in contact with one another are shorter or longer than illustrated. The maximum outer diameter 56 of the inner balloon 40 is smaller than the maximum cross-sectional area or outer diameter 80 of the outer balloon 42 in the expanded configuration. The maximum expanded outer diameter 80 of the outer balloon 42 is preferably at the middle portion 70 of the outer balloon 42, the cross-sectional area being large enough to dilate a portion of the body vessel when in the expanded configuration.

Additionally, the flow channel 168 significantly reduces the required pressure to infuse liquid and/or other therapeutic drugs through the outer balloon 42, thereby reducing the physical stress on the cells in cell therapy and other forms of medical treatment. Comparatively, other forms of weeping balloons without ridges, the required infusion pressure used to create a flow path between the pressurized inner balloon and the perforated outer balloon will be more or less identical to the inflation pressure of the inner balloon. In one particular application for cell therapy, if the infusion pressure has to be below 1 ATM, the inflation pressure of the inner balloon also need to be below same pressure. The flow channel 168 allows a higher inflation pressure of the inner balloon 40 to a range of about 2-8 ATM, depending on the number of ridges, without increasing the infusion pressure.

The outer balloon 42 is preferably shaped and configured for the intended use in a body vessel. When configured for use in a peripheral blood vessel, the expanded outer diameter 80 of the outer balloon 42 can be about 1.5 mm to about 8 mm, yet when configured for coronary vascular applications, the expanded outer diameter 80 can have a range from about 1.5 mm to about 4 mm. When configured for use in bile ducts, the expanded outer diameter 80 of the outer balloon 42 can be about 5-15 mm with a length of approximately 15-60 mm.

According to FIGS. 2A, 2B, 2C and 3, the annular balloon fluid delivery lumen 44 is defined as the space between the inner balloon 40 and the outer balloon 42. The working region of the annular balloon fluid delivery lumen 44 is the space between the body portion 50 of the inner balloon 40 and the middle portion 70 of the outer balloon 42 and the space between the proximal and the distal end portions 114 and 116 of the inner balloon 40 and the outer balloon 42. The annular balloon fluid delivery lumen 44 is in fluid communication with the fluid delivery lumen 33, shown within a tubular member 35 of the catheter shaft 22.

The annular balloon fluid delivery lumen 44 has a constant cross-sectional area along a first portion 90 and a second portion 92 of the longitudinal axis 24 moving distally. The second portion 92 of the annular balloon fluid delivery lumen 44 is similar to the cross-sectional area along the first portion 90. Alternatively, the second portion 92 of the annular balloon fluid delivery lumen 44 may have an increasingly larger cross-sectional area along the longitudinal axis 24 moving in the distal direction. As such, the change in cross-sectional area of the second portion 92 of the annular balloon fluid delivery lumen 44 can be inversely proportional to the tapering rate of the distal end portion 116 of the inner balloon 40.

The holes 46 for releasing fluid from the fluid delivery lumen 33 of the catheter shaft 22 can be disposed around the middle portion 70 of the outer balloon 42. The plurality of holes 46 can have any suitable size and shape suitable to provide a desired rate of fluid release from the annular balloon fluid delivery lumen 44. Preferably, the plurality of holes 46 has a uniform dimension of about 10 micrometer (0.0004 inch) to about 1 mm (0.04 inch). The holes can be formed by any suitable method including mechanical punching, laser cutting, and the like.

The inner balloon 40 and the outer balloon 42 can be formed and/or molded from a semi-compliant expandable, biocompatible material. Preferably, the inner balloon 40 and the outer balloon 42 are formed from the materials having a similar Young's modulus and expandability for better maintaining the space between the balloons during the entire inflation period. For example, the balloons 40, 42 can be formed from a polyamide (e.g., nylon 12) material, a polyamide block copolymer (e.g., PEBA) and blends thereof (e.g., nylon 12/PEBA and PEBA/PEBA blends). Alternative materials include polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel). The balloons 40, 42 can comprise any suitably non-elastic material such as ionomers, copolyesters, rubbers, or any medical grade polymers suitable for use in forming catheter balloons.

A proximal seal 82 and a distal seal 84 of the inner balloon 40 and a proximal seal 86 and a distal seal 88 of the outer balloon 42 can be formed in any suitable manner. Typically, the proximal and distal inner surfaces of the balloons 40, 42 are sealably attached to the catheter shaft 22 and/or tubular members to prevent any leakage of any fluid. Means of sealing the balloons 40, 42 include, for example, heat sealing, using an adhesive to form the seal, forced convection heating, radio frequency heating, ultrasonic welding, and laser bonding. Shrink tubing can be used as a manufacturing aid to compress and fuse each balloon 40, 42 to the catheter shaft 22 or the tubular member defining the wire guide lumen 38, the inflation lumen 30, and/or the fluid delivery lumen 33. The shrink tubing can be removed and disposed of after each balloon 40, 42 is sealed or can remain on as part of the connected structure. If the catheter shaft 22 has an outer coating, each balloon 40, 42 can be bonded to the coating or directly to the catheter shaft 22.

The therapeutic agent can be delivered through the fluid delivery lumen 33 and through the annular balloon fluid delivery lumen 44 at a pressure effective to deliver the therapeutic agent to the wall of the body vessel through the holes 46 in the outer balloon 42. The therapeutic agent can be delivered by direct local administration to the vessel site or injury through the holes 46 in the outer balloon 42. The antisense compound can have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily be 100% complementary to the target sequence, it is preferably effective to stably and specifically bind to the target sequence such that expression of the target sequence is modulated. The appropriate length of the oligomer to allow stable, effective binding combined with good specificity is about 8 to 42 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20 mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the therapeutic agent is a morpholino antisense compound having (i) from 8 to 42 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These therapeutic agents are described in U.S. Pat. No. 7,094,765 and published U.S. patent application US 2006/0269587 A1, which are incorporated herein by reference in their entirety. While the therapeutic agent is described with respect to certain preferred antisense compounds, any suitable therapeutic agent in fluid form (i.e., a gas and/or a liquid) or in a fluid carrier can be delivered from the multiple balloon catheter assembly 20.

Referring to FIG. 1, in operation, the multiple balloon assembly 20 of the multiple balloon catheter 10 can be implanted within a body vessel by conventional medical procedures, such as the Seldinger technique, and subsequently translated through the body vessel over the wire guide 36 through the wire guide lumen 38 to position the distal region at a point of treatment therein. Once implanted, the inner balloon 40 can be inflated to a desired diameter by injecting a suitable inflation fluid, such as a pressurized air, gas, or liquid, through the inflation port in the manifold. For example, the inner balloon 40 can be inflated to expand a stenosis in a body vessel such as a coronary artery.

A fluid containing a therapeutic agent and/or a diagnostic agent (e.g., x-ray contrast media) or any other fluid known to be used in a body vessel can be injected through the injection port, transported within the fluid delivery lumen 33 included in the catheter shaft 22 and introduced to the annular balloon fluid delivery lumen 44 between the outer balloon 42 and the inner balloon 40. The therapeutic agent fluid can be pressurized to deliver the therapeutic agent to the wall of the body vessel through the plurality of holes 46 in the inner balloon 40 before, during, or after inflation of the inner balloon 40.

Optionally, the multiple balloon assembly 20 of the multiple balloon catheter 10 can include radiopaque material to provide a means for locating the multiple balloon catheter 10 within a body vessel. For example, the catheter shaft 22 can include one or more marker bands annularly disposed around the outside of the catheter shaft 22 within the inner balloon 40 to define the weeping region of the multiple balloon catheter 10, or where the fluid is desirable to release to the body vessel. If desired, radiopaque bands can be added to the catheter shaft 22. Radiopaque marker bands can be used by a clinician to fluoroscopically view and locate the distal portion of the multiple balloon catheter 10 at a point of treatment within a body vessel. Various configurations of radiopaque marker bands can be used. For example, the radiopaque marker band can be located on a distal end and/or on the catheter shaft 22 within the inner balloon 40. The radiopaque marker bands can be stripes. Such radiopaque markers can be constructed by encapsulating a radiopaque material, such as a metallic ring, within the material of catheter shaft 22. Alternatively a portion of the catheter shaft 22 can be made radiopaque for example by constructing the portion from a radiopaque polymer. For example a polymer can be mixed with a radiopaque filler such as barium sulfate, bismuth trioxide, bismuth subcarbonate, or tungsten. The radiopaque material can comprise any suitable opacifying agent, further including bismuth, tantalum, or other suitable agents known in the art. The concentration of the agent in the coating can be selected to be adequately visible under fluoroscopy.

In another embodiment, methods of delivering a therapeutic agent to a body vessel are provided using any suitable catheter configuration, including the catheter of FIG. 3. Preferably, the methods include the step of inserting into a body vessel a multiple balloon catheter. For example, the multiple balloon catheter can include: (i) a catheter shaft extending from a proximal end to a distal end and defining an inflation lumen adjacently spaced from a fluid delivery lumen and a wire guide lumen; (ii) a deflated first balloon mounted on the distal end of the catheter shaft in communication with the inflation lumen, the first balloon having a constant cross-sectional area along a middle region between a first end and a second end; and (iii) a deflated second balloon mounted around at least a portion of the first balloon on the distal end of the catheter shaft in communication with the fluid delivery lumen, the second balloon having a middle portion including a plurality of holes in communication with the fluid delivery lumen for releasing a therapeutic agent from the fluid delivery lumen, where an annular balloon fluid delivery lumen is defined between the first balloon and the second balloon and in communication with the fluid delivery lumen. Optionally, the multiple balloon catheter can be translated through the body vessel over a wire guide slidably extending through the wire guide lumen to a point of treatment. The first balloon can be inflated at the point of treatment to place the second balloon in contact with the wall of the body vessel.

Figure 9:
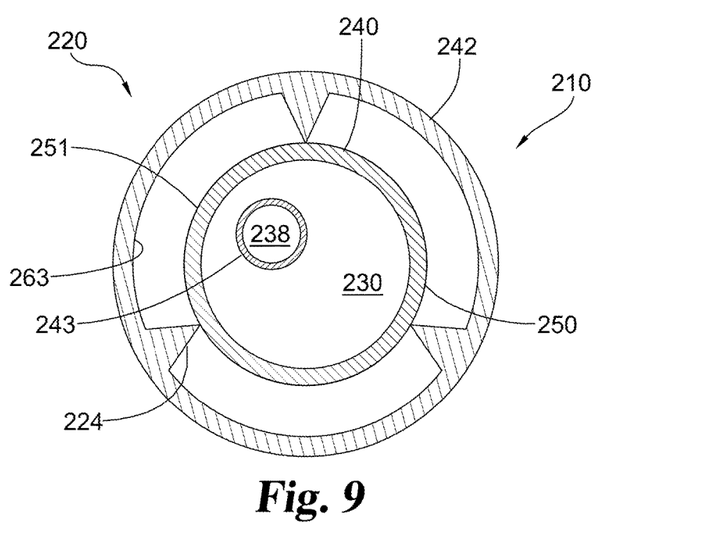
FIG. 9 is a transverse cross-sectional view of a multiple balloon catheter.

Illustrated in FIG. 9 is a multiple balloon catheter 210 that includes a multiple balloon assembly 220 having an outer balloon 242 radially disposed around an inner balloon 240. Multiple balloon assembly 220 is similar to multiple balloon assembly 20; therefore, for the sake of brevity similar features will not be described. The outer balloon 242 includes a plurality of ridges 224 which extend along a middle portion 250 of the inner balloon 240. In the illustrated embodiment, there are three ridges 224, although there could be one, two, or more than three in other embodiments. The ridges 224 extend substantially linearly along the axis of the balloon and are substantially equally spaced around the inner circumference of the outer balloon 242. The ridges 224 are placed on an interior surface 263 of the outer balloon 242 and extend to contact an outer surface 251 of an inner balloon 240 to create an inflation lumen 230. The inner balloon 240 defines the inflation lumen 230 extending radially around the tubular member 243 that defines the wire guide lumen 238.

Those of skill in the art will appreciate that other embodiments and variants of the structures and methods described above can be practiced within the scope of the present invention. It is therefore intended that the foregoing detailed description be regarded as illustrative rather than limiting, and that it be understood that it is the following claims, including all equivalents, that are intended to define the spirit and scope of this invention.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A method of forming a multiple-balloon intraluminal fluid delivery catheter for delivering a fluid into a body vessel, comprising:
   extruding a tube and a plurality of ribs through a die to form a monolithic single element that has a length that spans between a first end and a second end with the plurality of ribs extending along the length of the tube, the plurality of ribs defining a corresponding number of a plurality of channels that extend along the length of the tube;
   positioning a portion of the tube into a mold, the mold having a corresponding number of grooves sized and positioned to receive the plurality of ribs on the tube;
   constricting a proximal end portion near the first end and a distal end portion near the second end of the portion of the tube that is positioned in the mold;
   inflating the tube to produce an inner balloon, the inner balloon having a body portion that spans between the proximal end portion and the distal end portion;
   cutting the inner balloon near the proximal end portion and near the distal end portion to separate the inner balloon from a remainder of the tube; and
   disposing an outer balloon around the inner balloon, the outer balloon being movable between a compressed configuration and an expanded configuration, the outer balloon including a plurality of holes.

2. A method according to claim 1, further comprising: aligning the plurality of holes of the outer balloon with the plurality of channels on the inner balloon.

3. A method according to claim 1, further comprising: heating the portion of the tube in the mold; and stretching the portion of the tube in the mold.

4. A method according to claim 1, wherein the constricting includes radially compressing the proximal end portion and the distal end portion.

5. A method according to claim 1, further comprising: mounting the inner balloon on a catheter shaft; and mounting the outer balloon around at least a portion of the inner balloon.

6. A method according to claim 1, further comprising: reducing the height of the plurality of ribs by a linear amount along the proximal end portion and the distal end portion to reduce the stiffness of the plurality of ribs.

7. A method according to claim 6, wherein the reducing the height of the plurality of ribs includes laser cutting or grinding a portion of each of the plurality of ribs.

8. A method according to claim 6, wherein the reducing the height of the plurality of ribs occurs while the inflating the tube to produce the inner balloon.

9. A method according to claim 6, wherein the cutting the inner balloon occurs before the reducing the height of the plurality of ribs.

10. A multiple balloon intraluminal fluid delivery catheter for delivering a fluid into a body vessel comprising:
   a catheter shaft extending along a longitudinal axis from a proximal end to a distal end, the catheter shaft including an inflation lumen to deliver an inflation fluid and a fluid delivery lumen to deliver said fluid;
   an inner balloon when in an inflated configuration having a middle portion that spans between a proximal end portion that tapers from the middle portion to a proximal balloon neck and a distal end portion that tapers from the middle portion to a distal balloon neck, the inner balloon having an exterior surface with a plurality of ridges thereon that together span longitudinally from the proximal end portion to the distal end portion, each of the plurality of ridges including a ridge section on the proximal end portion of the inner balloon, a ridge section on the middle portion of the inner balloon, and a ridge section on the distal end portion of the inner balloon, each of the plurality of ridges having a height that is constant along the middle portion of the inner balloon, the inner balloon mounted on the distal end of the catheter shaft and in communication with the inflation lumen, the inner balloon being movable between a deflated configuration and the inflated configuration;
   an outer balloon mounted around the inner balloon, the outer balloon having a middle portion that spans between a proximal end and a distal end, the outer balloon being movable between a compressed configuration and an expanded configuration, the outer balloon including a plurality of holes; and
   the inner balloon and the outer balloon being configured and oriented such that a plurality of flow channels are defined when the inner balloon is in the inflated configuration and the outer balloon is in the expanded configuration and a portion of each of the plurality of ridges that spans along the middle portion engage an inner surface of the outer balloon, the inflated configuration of the inner balloon and the expanded configuration of the outer balloon defines an annular lumen there between, the annular lumen and the plurality of flow channels being in communication with the fluid delivery lumen and the plurality of holes such that the annular lumen and the plurality of flow channels are configured to promote delivery of said fluid through the plurality of holes, the annular lumen having a constant cross-sectional area along the longitudinal axis.

11. The multiple balloon intraluminal fluid delivery catheter of claim 10, wherein the ridge sections along the middle portion of the inner balloon engage the inner surface of the outer balloon.

12. The multiple balloon intraluminal fluid delivery catheter of claim 10, wherein the ridge sections along the middle portion, the proximal end portion, and the distal end portion of the inner balloon engage the inner surface of the outer balloon.

13. The multiple balloon intraluminal fluid delivery catheter of claim 10, wherein the plurality of holes are uniformly spaced along the longitudinal axis.

14. The multiple balloon intraluminal fluid delivery catheter of claim 10, wherein the plurality of flow channels have a constant cross-sectional area along the longitudinal axis.

15. The multiple balloon intraluminal fluid delivery catheter of claim 10, wherein the ridge sections on the proximal end portion of the inner balloon decrease in height in a direction toward the proximal balloon neck, and the ridge sections on the distal end portion of the inner balloon decrease in height in a direction toward the distal balloon neck.

16. The multiple balloon intraluminal fluid delivery catheter of claim 10, wherein the ridge sections on the proximal end portion of the inner balloon extend along the entire proximal end portion of the inner balloon, and wherein the ridge sections on the distal end portion of the inner balloon extend along the entire distal end portion of the inner balloon.

17. The multiple balloon intraluminal fluid delivery catheter of claim 10, wherein the ridge sections on the proximal end portion of the inner balloon extend only partially along the proximal end portion of the inner balloon, and wherein the ridge sections on the distal end portion of the inner balloon extend only partially along the distal end portion of the inner balloon.

18. The multiple balloon intraluminal fluid delivery catheter of claim 15, wherein the ridge sections on the proximal end portion of the inner balloon extend along the entire proximal end portion of the inner balloon, and wherein the ridge sections on the distal end portion of the inner balloon extend along the entire distal end portion of the inner balloon.

19. The multiple balloon intraluminal fluid delivery catheter of claim 15, wherein the ridge sections on the proximal end portion of the inner balloon extend only partially along the proximal end portion of the inner balloon, and wherein the ridge sections on the distal end portion of the inner balloon extend only partially along the distal end portion of the inner balloon.

* * * * *